United States Patent [19]

Yoshida et al.

[11] Patent Number: 5,068,019

[45] Date of Patent: Nov. 26, 1991

[54] ELECTROPHORESIS FILM SUPPORT

[75] Inventors: Takashi Yoshida; Tsueno Kawase; Nobuo Hiratsuka, all of Saitama, Japan

[73] Assignee: Fuji Photo Film Co., Ltd., Minami, Japan

[21] Appl. No.: 525,963

[22] Filed: May 18, 1990

[30] Foreign Application Priority Data

May 19, 1989 [JP] Japan .................................. 1-126286
May 19, 1989 [JP] Japan .................................. 1-126287

[51] Int. Cl.$^5$ .......................... C25B 1/00; C25B 7/00; B01D 61/42
[52] U.S. Cl. ............................... 204/182.8; 204/299 R
[58] Field of Search ............. 204/182.7, 182.8, 299 R

[56] References Cited

U.S. PATENT DOCUMENTS 4,128,470 12/1978 Hiratsuka ......................... 204/182.7

OTHER PUBLICATIONS

Patent Abstracts of Japan, vol. 10, No. 140 (P-458)(2197), 5/23/86 and JP-A-60 259 945 (Shimazu Seisakusho KK) 12/23/85.

Primary Examiner—John Niebling
Assistant Examiner—Caroline Koestner
Attorney, Agent, or Firm—McAulay Fisher Nissen Goldberg & Kiel

[57] ABSTRACT

An electrophoresis film support particularly useful for the electrophoretic separation of serum proteins. According to one aspect, the electrophoresis film support comprises a microporous polymer membrane sheet containing therein an additive which is selected from the group consisting of hydroxypropyl cellulose, triphenyl phosphate, tricresyl phosphate and mixtures thereof. According to another aspect the electrophoresis film support comprises a microporous membrane sheet made of a polymer material containing therein an additive which is selected from the group consisting of higher fatty acids having 10 to 27 carbon atoms and mixtures thereof, the additive being contained in an amount, based on the weight of the polymer material, ranging from 10 ppm to 3,000 ppm or the maximum solubility limit of the higher fatty acids in the polymer material.

9 Claims, 1 Drawing Sheet

ELECTROPHORESIS FILM SUPPORT

BACKGROUND OF THE INVENTION

1. Field of the Invention

The present invention relates generally to an electrophoresis film support made of a microporous polymer membrane sheet, and particularly to such a film support which is particularly suited for the separation of serum proteins.

2. Prior Art Statement

The electrophoresis has been used for the separation or purification of colloidal particles or macro molecules with a net electric charge as a method particularly useful for the separation or fractionation of proteins. The known electrophoreses include, in addition to the ordinary electrophoresis, the disc-electrophoresis in which a discontinuous buffer solution system is used for effecting the aimed separation, the immuno-electrophoresis in which separation and/or detection is effected by the utilization of immuno-diffusion reactions, the isoelectric focusing method wherein a certain pH gradient is established between both electrodes so that the aimed separation or fractionation is effected in the electric field having the thus established pH gradient.

In the field of clinical test, it is needed sometimes to fractionate the serum proteins, and for this purpose, various electrophoresis film supports made of microporous films mainly composed of polymer materials have been developed and used.

For example, such a microporous polymer film support film made of cellulose acetate is used in a method for the electrophoretic fractionation of serum proteins, the method comprising the steps of dipping the microporous film support in a buffer having a concentration of 0.03 to 0.08 mole/l and pH value of 8.6, spotting the serum on the surface of the microporous film, applying a DC current through the film to subject the proteins to electrophoresis for fractionating the same, and finally dyeing the separated proteins. Typical dyes used for dyeing the proteins include Ponceau-3R, Ponceau-S, Nigrosine, Amido Black and Coomassie-brilliant Blue. In general, the figure of the thus fractionated and dyed proteins includes five fractions which are referred to as the albumin fraction, the $\alpha_1$-globulin fraction, the $\alpha_2$-globulin fraction, the $\beta$-globulin fraction and the $\gamma$-globulin fraction.

The serum proteins are fractionated into five fractions, as described above. However, it is to be noted that each of these five fractions is not composed of a single chemical species but includes those which have incidentally the same mobility but have utterly different chemical structures. For example, the $\beta$-globulin fraction contains co-existent LDL (low density lipoprotein) which is a complex of choresterol (free chresterol and ester-form choresterol) and apo-protein (Content: about 18% to about 22% in dry weight base), other than the globulin component.

On the other hand, the $\alpha_2$-globulin fraction contains VLDL (very low density lipoprotein) which is a complex of choresterol (free chresterol and ester-form choresterol) and apo-protein (Content: about 6% to about 10% in dry weight base), other than the globulin component.

The fractionation is not a method by which the serum proteins are fractionated or separated into five series of fractions simply and clearly in respect of their chemical structures, but has been carried out, as a first or primary screening step for various clinical tests, to separate the serum proteins into five fractions to ascertain that the result of fractionation pattern is not significantly different from the result of fractionation pattern of normal serum proteins. It is an ordinary practice that a further precise examination on the serum proteins should be carried out when an abnormality is found by the test result of the primary screening, i.e. observation on the five fractions.

In recent years, the results of various examinations are often stored in a computer and read by putting out the data in the digital or analog fashion. Although such an automatic processing method has a merit that the data can be read to diagnose the condition of a particular patient more precisely, it has such disadvantages that confusion in pattern recognition by the automatic preocessing might be lead due to appearance of a superfluous peak or irregularization of the pitches or spacings between adjacent peaks which might be caused even by slight change in composition of the serum proteins to be fractionated into five fractions, leading to erroneous test result. Accordingly, there is a demand for the development of an electrophoresis film support having an ability for fractionating almost all of various serums into five fractions which may be easily identified, when the film support is used for the primary screening purpose, nonetheless more or less change in composition or irregularily of peak pitches might be present.

On the other hand, the positions of VLDL and LDL (commonly referred to as "pre-$\beta$-lipoprotein and $\beta$-lipoprotein, respectively) in the fractionation chart are shifted depending on the contents thereof. For example, a $\beta$-lipoprotein fraction (the sixth fraction) appears between the $\alpha_2$-globulin fraction (the third fraction) and the $\beta$-globulin fraction (the fourth fraction), and the position of this $\beta$-lipoprotein fraction is shifted depending on the content of $\beta$-lipoprotein within the spacing between the $\alpha_2$-globulin fraction (the third fraction) an $\beta$-globulin fraction (the fourth fraction). In detail, when the content of the $\beta$-lipoprotein is small the $\beta$-lipoprotein fraction is contained in the $\alpha_2$-glubulin fraction, but the same forms an independent peak between the $\alpha_2$-globulin fraction and the $\beta$-globulin fraction when the content of $\beta$-lipoprotein is large. Appearance of such sixth fraction hinders the analysis of the test result, since the test is normally based on the fractionation chart including five fractions.

The such hindrance on the analysis or diagnosis could be partially solved by the provision of an electrophoresis film support composed of a microporous polymer membrane sheet having a pore size distribution of from 0.1 $\mu$m to 2.0 $\mu$m disclosed, for example, by Unexamined Japanese Patent Publication No. 262549/1988 (Chemical Abstracts, 111: 112010v (1989)), or the provision of an electrophoresis film support composed of a microporous polymer membrane containing less than 20%, based on the weight of the polymer, of a particular wetting agent or plasticizer as disclosed by Unexamined Japanese Patent Publication No. 262550/1988 (Chemical Abstracts, 111: 112009b (1989)). However, the problem has not been fully solved by the use of the film supports disclosed by the prior publications. In addition, the problem of irregularity between the adjacent peaks of separated protein fractions has not been solved by the film supports of the publications referred to above.

OBJECTS AND SUMMARY OF THE INVENTION

An object of this invention is to provide an electrophoresis film support which for use to fractionate various serums.

Another object of this invention is to provide an electrophoresis film support on which a superferouns peak due to appearance of the sixth fraction of $\beta$-lipoprotein or irregularity of the spacings between adjacent peaks of separated proteins is not found, particularly when a serum containing a large quantity of $\beta$-lipoprotein is fractionated thereon.

A further object of this invention is to provide an electrophoresis film support on which unsatisfactory separation due to the shift of the peak position of the $\beta$-lipoprotein is not resulted even when a serum containing a large quantity of $\beta$-lipoprotein is fractionated.

A still further object of this invention is to provide an electrophoresis film support on which an electrophoresis image having a high contrast can be obtained by reducing the height of the minimum point between the peak of the $\alpha_2$-globulin fraction and the peak of the $\beta$-globulin fraction.

Yet a further object of this invention is to provide an electrophoresis film support which is easily handled in a substantially dried state.

A more specific object of this invention is to provide an electrophoresis film support composed of a microporous polymer film which is improved over those disclosed by Unexamined Japanese Patent Publication Nos. 62549/198 (Chemical Abstracts 111: 112010v (1989)) and 652550/1988 (Chemical Abstracts 111: 112009b (1989)).

According to a first aspect of this invention, the objects of this invention is achieved by the provision of an electrophoresis film support comprising a microporous polymer membrane sheet containing therein an additive which is selected from the group consisting of hydroxypropyl cellulose, triphenyl phosphate, tricresyl phosphate and mixtures thereof.

On the film support, provided in accordance with the first aspect of this invention, the sixth peak of $\beta$-lipoprotein does not appear to give a franctionation pattern having clear five fractions to realize improvement in effectiveness in separation.

According to a second aspect of this invention, the aforementioned objects of this invention is achieved by the provision of an electrophoresis film support comprising a microporous membrane sheet made of a polymer material containing therein an additive which is selected from the group consisting of higher fatty acids having 10 to 27 carbon atoms and mixtures thereof, said additive being contained in an amount, based on the weight of said polymer material, ranging from 10 ppm to 3,000 ppm or the maximum solubility limit of said additive in said polymer material.

BRIEF DESCRIPTION OF THE DRAWINGS

The above objects and advantages of the invention becomes apparent from the following description of preferred embodiments taken in conjugation with the appended drawings, in which.

DESCRIPTION OF PREFERRED EMBODIMENTS

Figure 1:
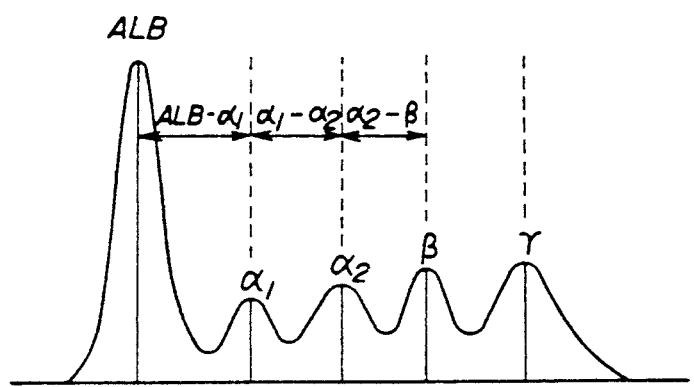
FIG. 1 is a chart showing the change in optical density of a dyed electrophoresis pattern which is obtained by the electrophoresis of human serum on each of the microporous films used in Examples 1 to 3 of the invention and Comparative Example 1 (prior art technology), the curve in the chart containing peaks for the serum protein components albumin (ALB), $\alpha_1$-globulin ($\alpha_1$), $\alpha_2$-globulin ($\alpha_2$), $\beta$-globulin ($\beta$) and $\gamma$-globulin ($\gamma$) with respective spacings between adjacent peaks.

The elctrophoresis film support, according to this invention, is an improvement of the electrophoresis film support described in Japanese Patent Publication No. 31418/1980 (corresponding to U.S. Pat. No. 4,128,470 and GB 1,519,385A) and Unexamined Japanese Patent publication Nos. 262549/1988 (Chemical Abstracts 111: 112010v (1989)) and 262550/1988 (Chemical Abstracts, 111: 112009b (1989)). According to the first aspect of the invention, electrophoresis film support is characterized by containing an additive selected from the group consisting of hedroxypropyl cellulose, triphenyl phosphate, tricresyl phosphate or mixtures thereof. According to the second aspect, the additive is one or more of fatty acids each having 10 to 27 carbon atoms including the carbon atom of the carboxyl group.

The electrophoresis film support made of microporous polymer membrane sheet, according to the invention, is a substantially dried membrane or film having a thickness of from about 50 $\mu$m to about 300 $\mu$m, preferably from about 100 $\mu$m to about 150 $\mu$m. The pore size of the micro pores ranges from about 0.1 $\mu$m to about 10 $\mu$m, preferably from about 0.1 $\mu$m to about 2 $\mu$m. The porosity of the microporous film ranges from about 50% to about 90%, preferably from about 60% to about 85%.

The electrophoresis film support of the invention may be prepared generally in accordance with the known method described in Japanese Patent Publication No. 31418/1980 (corresponding to U.S. Pat. No. 4,1282,470 and GB 1,519,385A) and Unexamined Japanese Patent Publication No. 122565/1975(corresponding to U.S. Pat. No. 4,171,987). The disclosures in these prior publications will be incorporated herein as references.

Examples of the polymer material, from which the microporous polymer membrane sheet is prepared, include cellulose esters such as nitrocellulose, cellulose acetate (cellulose diacetate and cellulose triacetate), cellulose acetate butylate and cellulose propionate; polyamide resins; and polyvinyl chloride resin. One of these polymer materials may be used singly, or two or more of them may be used in combination. Amongst these polymer materials, cellulose esters and polyamide resins are preferable and the most preferable material is cellulose acetate (cellulose diacetate or cellulose triacetate).

The hydroxypropyl cellulose which may be used as the additive in the invention includes those having a content of hydroxypropyl group ranging from about 55% to about 75%, based on the hydroxyl groups of cellulose. Any one of hydroxypropyl cellulose, triphenyl phosphate or tricresyl phosphate may be used singly, or two or three of these compounds may be used together. The content of hydroxypropyl cellulose, triphenyl phosphate and/or tricresyl phosphate ranges generally from about 0.1 wt% to about 3.0 wt%, preferably from about 0.2 wt% to about 2.5 wt%, bases on the weight of the polymer material from which the microporous polymer membrane sheet is prepared.

The higher fatty acids each having 10 to 27 carbon atoms, including the carbon atom of the carboxyl group, which may be used as the additive according to the second aspect of this invention include straight chain or branched chain saturated carboxylic acids represented by the general formula of $C_nH_{2n+1}COOH$ (wherein n stands for an integer of from 9 to 26). Any one of the higher fatty acids represented by the general formula set forth above may be used singly, or two or more than three of them may be used in combination. The content of the higher fatty acid ranges from about 10 ppm to about 3,000 ppm (from about 10 ppm to the maximum solubility limit when a fatty acid having a solubility limit of less than 3,000 ppm is used), preferably from about 10 ppm to about 1,000 ppm (from about 10 ppm to the maximum solubility limit when a fatty acid having a solubility limit of less than 1,000 ppm is used), based on weight of the polymer material used for forming the microporous polymer membrane sheet.

Specific examples of the fatty acids and preferable contents thereof will be set forth below. (The number of carbon atoms including the carbon atom of carboxyl group is denoted by the number following to the latter C; and the fatty acids other than isostearic acid is straight chain fatty acids.)

Decanoic Acid (n-Capric Acid), C10, from about 500 ppm to about 1,000 ppm;

Hendecanoic Acid (Undecylic Acid), C11, from about 500 ppm to about 1,000 ppm;

Dodecanoic Acid (Lauric Acid, C12, from about 500 to about 1,000 ppm;

Tridecanoic Acid (Tridecylic Acid), C13, from about 500 ppm to about 1,000 ppm;

Tetradecanoic Acid (Cylistyric Acid), C14, from about 500 ppm to about 1,000 ppm;

Pentadecanoic Acid (Pentadecylic Acid), C15, from about 500 ppm to about 1,000 ppm;

Hexadecanoic Acid (Palmitic Acid), C16, from about 500 ppm to about 1,000 ppm;

Heptadecanoic Acid (Margaric Acid), C17, from about 100 ppm to about 1,000 ppm;

Octadecanoic Acid (Stearic Acid), C18, from about 10 ppm to about 1,000 ppm;

Nonadecanoic Acid (Nonadecylic Acid), C19, from about 10 to about 1,000 ppm;

Eicosanoic Acid (Arachidic Acid), C20, from about 10 ppm to about 1,000 ppm;

Heneicosanoic Acid, C21, from about 10 ppm to about 1,000 ppm;

Docosanoic Acid (Behenic Acid), C22, from about 10 ppm to about 1,000 ppm;

Tricosanoic Acid, C23, from about 10 ppm to about 1,000 ppm;

Tetracosanoic Acid (Lignoceric Acid), C24, from about 10 ppm to about 1,000 ppm;

Pentacosanoic Acid, C25, from about 10 ppm to about 1,000 ppm;

Hexacosanoic Acid (Cerotic Acid), C26, from about 10 ppm to about 1,000 ppm;

Isostearic Acid, branched chain, C18, from about 10 ppm to about 1,000 ppm;

Heptacosanoic Acid, C27, about 10 ppm.

Amongst the higher fatty acids set forth above, preferable fatty acids are nonadecanoic acid (nonadecylic acid), eicosanoic acid (arachidic acid), heneicosanoic acid, docosanoic acid (behenic acid), tricosanoic acid, tetracosanoic acid (lignoceric acid), pentacosanoic acid and hexacosanoic acid (cerotic acid).

Any known plasticizer or wetting agent may be contained in the microporous polymer membrane sheet. Such a plasticizer or wetting agent is added so that the resultant microporous membrane sheet becomes soft, and the content thereof ranges from about 1 wt% to about 20 wt%, based on the weight of the polymer material. Specific examples of usable plasticizer or wetting agent include diols such as ethylene glycol, diethylene glycol, propylene glycol, tetramethylene glycol and glycerol monoacetyl ester; and glycerol, triethyl citrate, tributyl citrate, trimethyl citrate, diethyl oxalate, dipropyl oxalate, tributyrin (glycerol tributyrate), triacetin (glycerol triacetate), diethyl succinate and dibutyl succinate.

The process for the preparation of the microporous polymer membrane sheet will now be described. Initially, the polymer material, the additive (hydroxypropyl cellulose, triphenyl phosphate or tricresyl phosphate) and/or the higher fatty acid, optionally with the plasticizer or wetting agent, are dissolved substantially uniformly in a mixed solvent which will be described in detail hereinafter. The resultant solution was used to prepare a microporous membrane sheet generally following to the known procedure as described in the prior patent publications referred to above. For example, the uniform solution is flown over a tentative support having a smooth surface, followed by drying at a controlled temperature, and then the formed dry film is peeled off from the tentative support to obtain a microporous polymer membrane sheet.

The mixed solvent used in this process contains all of a good solvent, a poor solvent, and a non-solvent. The term "good solvent" as herein used means those solvents capable of dissolving the polymer material; the term "poor solvent" means those solvents which are mutually soluble with good solvents, do not substantially dissolve the polymer materials but only swell them, and have a higher boiling point than the good solvent; and the term "non-solvent" means those materials which are mutually soluble with good solvents or poor solvents, do neither dissolve nor swell the polymer materials, and have a higher boiling point than good solvents.

Specific examples of the good solvent include methylene chloride, acetone and methyl formate for cellulose acetate; diethyl ether, methyl acetate, acetone and acetic acid for nitrocellulose; and methanol and ethanol for polyamide resins.

Specific examples of the poor solvent include tetrahydrofuran and methanol for cellulose acetate; butanol and ethanol for nitrocellulose; and tetrahydrofuran, dioxane and ethyl acetate for polyamide resins.

As the non-solvent, water is often used.

However, classification of the good solvents, poor solvents and the non-solvents is not monistic, the process for the preparation of the electrophoresis film support, as described above, has been given for example only and should not be construed as limitative.

The solvents, particularly the good solvents and the poor solvents, may be used in the manner as described in Japanese Patent publication No. 31418/1980 (corresponding to U.S. Pat. No. 4,128,470) and Unexamined Japanese Patent publication Nos. 122565/1975 (corresponding to U.S. Pat. No. 4,171,987) and 76360/1976 (chemical Abstracts; 85, 161460v).

The poor size distribution of the microporous polymer membrane sheet used for the electrophoresis film support of this invention has been determined by the mercury press-in method described in E. W. Wash Bahn, "Proc. Natl. Acad. Sci., U.S.A.", No. 1, p1115 (1921); Tominaga Keii, "KYORITSU ZENSHO" Vol. 157 "Absorption", page 130; Renichi Kondo, "TAKO ZAIRYO" ("Porous Material") published by GIHODO (1973); and "KAGAKU KOGAKU" ("Chemical engineering"), Vol. 31, pp 60 to 66 (1967). The pore size distribution range is defined so that 97% of pores have a pore size of from about 0.1 μm to about 10 μm, preferably about 2.0 μm. The pore size distribution means that the pore size range corresponding to the cummulative ratio of 3% to 97% as the cummulative ratio is obtained by referring to the Pore size/cummulative Ratio Table established by the mercury press-in method.

EXAMPLES 1 TO 3 AND COMPARATIVE EXAMPLE 1

Preparation of Microporous Membrane Sheet

A substantially uniform solution having the following composition was prepared, and the solution was flown over a glass plate (temporary support) having a smooth surface to form a membrane sheet having a thickness of 1 mm. The membrane sheet was dried at 25° C. until the overall surface of the membrane sheet had a uniform white color, and then peeled off from the glass plate. The peeled-off membrane sheet was spread on a frame and dried at 100° C. for additional one hour to prepare a microporous membrane sheet. The thus formed microporous membrane sheet has a thickness at the dried state of about 150 um and a pore size range of 0.1 μm to 2.0 μm.

| Composition of Solution (* means the quantities as set forth in Table 1) | |
|---|---|
| Cellulose Triacetate (Content of Acetyl Group: 43.5%) | 30 g |
| Cellulose Diacetate (Content of Acetyl Group: 39.4%) | 30 g |
| Glycerol | 4.2 g |
| Tributyrin | 4.8 g |
| Triphenyl Phosphate | * |
| Methylene chloride | 600 g |
| Methanol | 280 g |
| Water | 40 g |
| Hydroxypropyl Cellulose (Content of Hydroxypropyl Group: 64.0%) | * |
| Methyl Cellulose (Content of Methoxy Group: 29.8%) | * |

TABLE 1

| Example 1 | Hydroxypropyl Cellulose | 300 mg |
|---|---|---|
| Example 2 | Hydroxypropyl Cellulose | 300 mg |
| | Triphenyl Phosphate | 1.2 g |
| Example 3 | Triphenyl Phosphate | 1.2 g |
| Comp. Ex. 1 | Methyl Cellulose | 200 mg |

Property Appraisal Test 1

Each of the four microporous membrane sheets as prepared by Examples 1 to 3 and Comparative Example 1 was cut into a piece having a size of 70 mm × 200 mm, and impregnated with a 0.07M diethyl barbital pH buffer solution having a pH value of 8.6 (the solution was prepared by dissolving 2.30g of diethyl barbital and 11.80g of sodium diethyl barbital in distilled water so that the resultant solution had total volume of 1000 ml at 25° C.). Each of the membrane sheets impregnated with the buffer solution was set in an electrophoresis apparatus filled with same buffer solution, and filter paper was placed on the membrane sheet as a salt bridge. Using a micropipette, a total volume of 0.1 μl of the human blood serum was spotted on each microporous membrane sheet along a linear line having a length of 10 mm at a position spaced from the terminal edge of the membrane sheet at a cathod end by 15 mm. 0.6 mA/cm of DC current was applied to the membrane sheet along the direction perpendicular to the linear spot line of the blood serum (i.e. along the line parallel to the width direction having a width of 70 mm) to subject the blood serum to electrophoresis. After the completion of electrophoresis, the membrane sheet was immersed in a Ponceau-3R dyeing solution (an aqueous dyeing solution having a composition containing 3g of Ponceau-3R, 6R of trichloroacetic acid and 91g of water), and then the film was rinsed with an aqueous solution of 1% acetic acid for four times, each rinsing operation being continued for 2 minutes.

Filter paper sheets were applied on both sides of the rinsed film to remove the rinsing solution, and then the film was dried in air.

After air drying, the electrophoresis pattern of the serum proteins was observed to confirm that the pattern had five protein fractions and did not have the sixth fraction of β-lipoprotein. The optical density change of the dyed electrophoresis pattern was measured through a densitometer to obtain a curve shown in FIG. 1, the curve having clear five peaks (respectively referred to as ALB, $\alpha_1$, $\alpha_2$, and $\beta$ and $\gamma$).

For the curve showing the optical density change of the electrophoresis pattern, as shown in FIG. 1, the separation ability will be defined as follows.

The spacings between the peaks ALB, $\alpha_1$, $\alpha_2$ and $\beta$ will be represented by relative ratios.

When the relative ratios of the spacings between adjacent peaks ALB, $\alpha_1$, $\alpha_2$ and $\beta$ are closer to 1:1:1, it is judged that the separation ability is high.

The improvement in separationability achieved by the use of the electrophoresis film support of the invention is an improvement in balance of respective spacings between the adjacent peaks ALB, $\alpha_1$, $\alpha_2$ and $\alpha$, and the balance can be appraised by representing the spacings between adjacent peaks by relative ratios which are compared with each other. In Table 2, the relative ratios of the spacings between adjacent peaks, (ALB$-\alpha_1$), ($\alpha_1-\alpha_2$) and ($\alpha_2-\beta$), for respective microporous films prepared by Examples 1 to 3 and Comparative Example 1 was tabulated. In Table 2, the values in the parentheses show the relative ratios of spacings between adjacent peaks when the minimum spacing between adjacent peaks is taken as the standard value (1.00).

As will be seen from Table 2, the relative ratios of spacings between respective adjacent peaks, (ALB$-\alpha_1$), ($\alpha_1-\alpha_2$) and ($\alpha_2-\beta$), found on the microporous membrane sheets (Examples 1 to 3) according to this invention are closer to the ratio of 1:1:1, as compared to those found on the microporous membrane sheet of Comparative Example 1, to reveal that the microporous membrane sheets of the invention have higher separationability as that obtainable by the conventional technology.

TABLE 2

|  | ALB-$\alpha_1$ | $\alpha_1$-$\alpha_2$ | $\alpha_2$-$\beta$ |
| --- | --- | --- | --- |
| Example 1 | 35 (1.16) | 35 (1.16) | 30 (1.00) |
| Example 2 | 34 (1.03) | 33 (1.00) | 33 (1.00) |
| Example 3 | 35 (1.16) | 35 (1.16) | 30 (1.00) |
| Comparative Ex. 1 | 37 (1.37) | 36 (1.33) | 27 (1.00) |

EXAMPLES 4 TO 22 AND COMPARATIVE EXAMPLE 2

Preparation of Microporous Membrane Sheet

A substantially uniform solution having the following composition was prepared, and the solution was flown over glass plate (temporary support) having a smooth surface to form a membrane sheet having a thickness of 1 mm. The membrane sheet was dried at 25° C. until the overall surface of the membrane sheet had a uniform white color, and then peeled off from the glass plate. The peeled-off membrane sheet was spread over a frame and dried at 100° C. for additional one hour to prepare a microporous membrane sheet. The thus formed microporous membrane sheet has a thickness at the dried state of about 150 μm and a pore size range of from 0.1 μm to 2.0 μm.

| Composition of Solution | |
| --- | --- |
| Cellulose Triacetate | 30 g |
| (Content of Acetyl Group: 43.5%) | |
| Cellulose Diacetate | 30 g |
| (Content of Acetyl Group: 39.4%) | |
| Glycerol | 4.2 g |
| Tributyrin | 4.8 g |
| Triphenyl Phosphate | 1.2 g |
| Methylene Chloride | 600 g |
| Methanol | 280 g |
| Water | 40 g |
| Hydroxypropyl Cellulose | 300 mg |
| (Content of Hydroxypropyl Group: 64.0%) | |

(Content of Hydroxypropyl Group: 64.0%) Higher Fatty Acid: Each of following compounds was added in an amount of 10 ppm, 100 ppm and 1,000 ppm based on the total weight of cellulose triacetate and cellulose diacetate. (The number of carbon atoms including the carbon atom of carboxylic group is denoted by the number following to the letter C.)

Example 4: Decanoic Acid (n-Capric Acid), Straight Chain, C10
Example 5: Hendecanoic Acid (Undecylic Acid), Straight Chain, C11
Example 6: Dodecanoic Acid (Lauric Acid), Straight Chain, C12
Example 7: Tridecanoic Acid (Tridecylic Acid), Straight Chain, C13
Example 8: Tetradecanoic Acid (Cylistylic Acid), Straight Chain, C14
Example 9: Pentadecanoic Acid (Pentadecylic Acid), Straight Chain, C15
Example 10: Hexadecanoic Acid (palmitic Acid), Straight Chain, C16
Example 11: Heptadecanoic Acid (margaric Acid), Straight Chain, C17
Example 12: Octadecanoic Acid (Stearic Acid), Straight Chain, C18
Example 13: Nonadecanoic Acid (Nonadecylic Acid), Straight Chain, C19
Example 14: Eicosanoic Acid (Arachidic Acid), Straight Chain, C20
Example 15: Heneicosanoic Acid, Straight Chain, C21
Example 16: Docosanoic Acid (Behenic Acid), Straight Chain, C22
Example 17: Tricosanoic Acid, Straight Chain, C22
Example 18: Tetracosanoic Acid (Lignoceric Acid), Straight Chain, C24
Example 19: Pentacosanic Acid, Straight Chain, C25
Example 20: Hexaconic Acid (Cerotic Acid), Straight Chain, C26
Example 21: Isostearic Acid, Branched Chain, C18
Example 22: Heptacosanic Acid, Straight Chain, C27
Comparative Example 2: No Higher Fatty acid added Property Appraisal Test 2

Each of the sixty microporous membrane sheets as prepared by Examples 4 to 22 and comparative Example 2 was cut into a piece having a size of 70 mm×200 mm, and impregnated with a 0.07M diethyl barbital pH buffer solution having a pH value of 8.6 (the solution was prepared by dissolving 2.30g of diethyl barbital and 11.80g of sodium diethyl barbital in distilled water so that the resultant solution had a total volume of 1,000 ml at 25° C.). Each of the membrane sheets impregnated with the buffer solution was set in an electrophoresis vessel filled with the same buffer solution, and filter paper was placed on the membrane sheet as a salt bridge. Using a micropipette, a total volume of 0.1 μl of the human blood serum was spotted on each microporous membrane sheet along a linear line having a length of 10 mm at a position spaced from the terminal edge of the membrane sheet at the cathode end by 15 mm. 0.6 mA/cm of DC current was applied to the membrane sheet along the direction perpendicular to the linear spot line of the blood serum (i.e. along the line parallel to the width direction having a width of 70 mm) to subject the blood serum to electrophoresis. After the completion of electrophoresis, the membrane sheet was immersed in a Ponceau-3R dyeing solution (an aqueous dyeing solution having a composition containing 3g of Ponceau-3R, 6g of trichloroacetic acid and 91g of water), and then the membrane sheet was rinsed with an aqueous solution of 1% acetic acid for four times, each rinsing operation being continued for 2 minutes.

Filter paper sheets were applied on both sides of the rinsed membrane sheet to remove the rinsing solution, and then the membrane sheet was dried in air.

After air drying, the electrophoresis pattern of the serum proteins was observed to confirm that the pattern had five protein fractions and did not have the sixth fraction of β-lipoprotein. The optical density change of the dyed electrophoresis pattern was measured through a densitometer to obtain a curve shown in FIG. 2, the curve having clear five peaks (respectively referred to as ALB, $\alpha_1$, $\alpha_2$, $\beta$ and $\gamma$).

Figure 2:
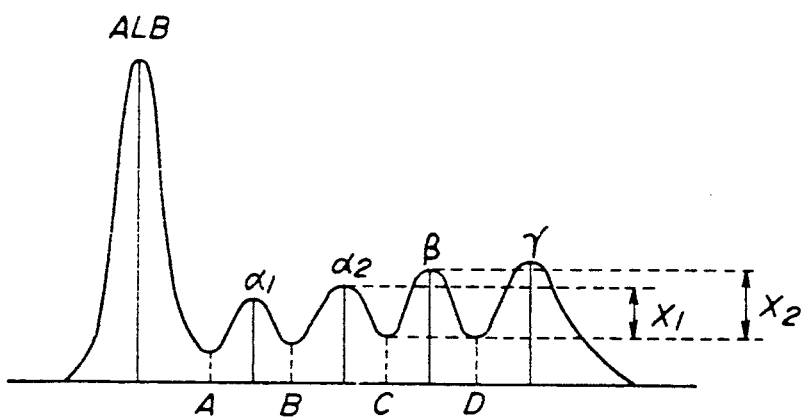
FIG. 2 is a chart showing the change in optical density of a dyed electrophoresis pattern which is obtained by the electrophoresis of human serum on each of the microporous films used in Examples 4 to 22 of the invention and Comparative Example 2 (prior art technology), the curve in the chart containing peaks for the serum protein components albumin (ALB), $\alpha_1$-globulin ($\alpha_1$), $\alpha_2$-globulin ($\alpha_2$), $\beta$-globulin ($\beta$) and $\gamma$-globulin ($\gamma$) separated with each other by respective spacing between adjacent peaks.

For the curve showing the optical density change of the electrophoresis pattern, as shown in FIG. 2, the separationability will be defined as follows.

The values $X_1$ and $X_2$ are calculated from the following equations by referring to the heights of the peaks $\alpha_2$ and $\beta$ and the minimum value C, and the separationability is defined as higher as the values $X_1$ and $X_2$ take higher values.

$X_1$ = Optical Density of the Peak $\alpha_2$ Optical Density of the Point C $X_2$ = Optical Density of the Peak $\beta$ Optical Density of the Point C The values $X_1$ and $X_2$ for the respective microporous membrane sheets prepared by Examples 4 to 22 and Comparative Example 2 are set forth in Table 3. It will seen from the data set forth in Table 3 that $X_1$ and $X_2$ of the microporous membrane sheets of the present invention take higher values as compared to $X_1$ and $X_2$ of the microporous membrane sheet of Comparative Example 2 to have higher separationability. Meanwhile, the data in Table 3 do not indicate the differences in optical densities but are relative values indicating the differences in distance in an arbitrary scale on the curve showing the change in optical density of the electrophoresis pattern. In Table 3, "-" indicates that the higher fatty acids were not dissolved.

TABLE 3

| Example No. | Added Amount of Fatty Acid | | | | | |
|---|---|---|---|---|---|---|
| | 10 ppm | | 100 ppm | | 1000 ppm | |
| | $X_1$ | $X_2$ | $X_1$ | $X_2$ | $X_1$ | $X_2$ |
| 4 | 1.0 | 1.0 | 1.1 | 1.1 | 1.6 | 1.6 |
| 5 | 1.2 | 1.3 | 1.4 | 1.4 | 2.0 | 2.0 |
| 6 | 1.2 | 1.2 | 1.5 | 1.5 | 2.3 | 2.3 |
| 7 | 1.4 | 1.4 | 1.5 | 1.6 | 2.4 | 2.4 |
| 8 | 1.5 | 1.6 | 1.6 | 1.6 | 2.4 | 2.5 |
| 9 | 1.5 | 1.6 | 1.6 | 1.6 | 2.4 | 2.5 |
| 10 | 1.6 | 1.7 | 1.6 | 1.7 | 2.5 | 2.5 |
| 11 | 1.6 | 1.7 | 1.6 | 1.7 | 2.5 | 2.5 |
| 12 | 1.6 | 1.6 | 2.1 | 2.1 | 2.5 | 2.6 |
| 13 | 2.0 | 2.1 | 2.2 | 2.2 | 2.5 | 2.6 |
| 14 | 2.1 | 2.2 | 2.2 | 2.3 | 2.5 | 2.6 |
| 15 | 2.2 | 2.2 | 2.2 | 2.3 | 2.5 | 2.6 |
| 16 | 2.2 | 2.2 | 2.2 | 2.3 | 2.5 | 2.6 |
| 17 | 2.2 | 2.2 | 2.2 | 2.3 | 2.5 | 2.6 |
| 18 | 2.1 | 2.2 | 2.2 | 2.3 | 2.5 | 2.5 |
| 19 | 2.1 | 2.2 | 2.2 | 2.3 | 2.5 | 2.5 |
| 20 | 2.0 | 2.1 | 2.2 | 2.2 | — | — |
| 21 | 2.6 | 1.6 | 2.2 | 2.2 | 2.4 | 2.5 |
| 22 | 1.6 | 1.7 | — | — | — | — |
| Comparative Example 2 | 0.8 | 0.9 | | | | |

Property Appraisal Test 3

Generally similar to the Property Appraisal Test 2, the electrophoresis pattern was dyed with Ponceau-3R and the dyed electrophoresis pattern was measured, and then the film was again dyed by the blue dyeing method wherein $\beta$-lipoprotein was dyed through the Ozonized Shiff's Process, followed by determination of the distance $\beta_L$-$\beta$) between the peak position ($\beta_L$) of $\beta$-lipoprotein and the peak position ($\beta$) of $\beta$-globulin. The results are shown in Table 4. The data in Table 4 indicate the distances (relative values) on the curve showing the optical density change of the electrophoresis patterns. In Table 4, "-" indicates that the higher fatty acids were not dissolved.

Since the films giving larger $X_1$ and $X_2$ in the preceding Property Appraisal Test 2 gave larger distances between the peak position of $\beta$-lipoprotein and the peak position of $\beta$-globulin, interference on the electrophoresis patterns by $\beta$-lipoprotein was eliminated to give clearly distinguishable peak positions of peaks $\alpha_2$ and $\beta$

TABLE 4

| Example No. | Added Amount of Fatty Acid | | |
|---|---|---|---|
| | 10 ppm $\beta_L$-$\beta$ | 100 ppm $\beta_L$-$\beta$ | 1000 ppm $\beta_L$-$\beta$ |
| 4 | 0.5 | 0.6 | 1.4 |
| 5 | 0.6 | 0.8 | 1.5 |
| 6 | 0.8 | 0.9 | 2.2 |
| 7 | 0.8 | 0.9 | 2.3 |
| 8 | 0.9 | 1.0 | 2.5 |
| 9 | 0.9 | 1.0 | 2.5 |
| 10 | 1.2 | 1.3 | 3.0 |
| 11 | 1.3 | 1.5 | 3.3 |
| 12 | 1.4 | 1.6 | 3.8 |
| 13 | 1.6 | 1.8 | 4.1 |
| 14 | 1.8 | 1.9 | 4.6 |
| 15 | 1.9 | 2.1 | 4.6 |
| 16 | 1.8 | 2.1 | 4.3 |
| 17 | 1.8 | 2.0 | 4.2 |
| 18 | 1.7 | 1.9 | 3.9 |
| 19 | 1.7 | 1.8 | 3.9 |
| 20 | 1.6 | 1.7 | — |
| 21 | 1.4 | 1.7 | 2.5 |
| 22 | 1.2 | — | — |
| Comparative Example 2 | 0.5 | | |

The blue dyeing method of $\beta$-lipoprotein through the Ozonized Shiff's Process will be described below.

(1) Preparation of Shiff's Dyeing Solution 13.7g of sodium pyrosulfite, 21 ml of conc. HCl and 8.0g of fuchsine were dissolved in distilled water, and the total volume of the solutiona was adjusted to 2000 ml and then the solution was stirred overnight. After adding five large spoons of activated carbon, the solution was filtered through filter paper over a period of 15 minutes, and then the filtrate was stored at a cold place maintained at about 4° C.

(2) Preparation of Shiff's Rinsing Solution 4.3g of sodium pyrosulfite and 9 ml of concentrated hydrochloric acid were dissolved in 885g of distilled water, and then added with 100 ml of 95% ethanol.

(3) Dyeing Operation

The membrane sheet dyed with Ponceau-3R and used for the measurement of the electrophoresis pattern in the Property Appraisal Test 2 was ozonized for 20 minutes in an ozone generator (produced by Nippon Ozon Co., Tokyo).

After dipping the ozonized membrane sheet in the Shiff's rinsing solution for a few seconds, the membrane sheet was dyed with the Shiff's dyeing solution over a period of 10 minutes, and then subjected to repeated three time rinsing operations each effected for 10 minutes by the Shiff's rinsing solution, and then the membrane sheet was dried by sandwitching it between filter papers.

While the invention has been described in detail by referring to specific embodiments and examples, it will be apparent to those skilled in the art that various modifications, alternations or changes can be made within the broadest scope of the invention as defined in the appended claims.

What is claimed is:

1. An electrophoresis film support for analysis of serum protein comprising a microporous polymer membrane sheet containing therein an additive which is selected from the group consisting of hydroxypropyl cellulose, triphenyl phosphate, tricresyl phosphate and mixtures thereof, and having the property that when used for serum protein analysis with a homogenous electrolyte buffer system which does not form a pH gradient on the film, the sixth peak of β-lipoprotein does not appear to give a frction pattern having clear five fractions.

2. The electrophoresis film support according to claim 1 wherein said additive is a mixture of
   (A) hydroxypropyl cellulose and
   (B) a phosphate selected from the group consisting of triphenyl phosphate, tricresyl phosphate and mixtures thereof.

3. In a method for the analysis of serum protein in a sample wherein the sample is deposited on a membrane sheet and is then subjected to electrophoresis, the improvement which comprises the membrane sheet being the electrophoresis film support of claim 1 and wherein the analysis is carried out such that a pH gradient does not exist on the film.

4. In a method for the analysis of serum protein in a sample wherein the sample is deposited on a membrane sheet and is then subjected to electrophoresis, the improvement which comprises the membrane sheet being the electrophoresis film support of claim 2 and wherein the analysis is carried out such that a pH gradient does not exist on the film.

5. The electrophoresis film support according to claim 1 wherein said microporous polymer membrane sheet is made of at least one polymer selected from the group consisting of cellulose esters, polyamides and polyvinyl chloride, and wherein the content of said additive in said polymer ranges from 0.1% to 3.0% by weight based on the weight of said polymer.

6. The electrophoresis film support according to claim 1, wherein said additive is hydroxypropyl cellulose, the content of hydroxylpropyl group in said hydroxypropyl cellulose ranging from 55 to 75%.

7. An electrophoresis film support comprising a microporous membrane sheet made of a polymer material containing therein an additive which is selected from the group consisting of higher fatty acids having 10 to 27 carbon atoms and mixtures thereof, said additive being contained in an amount, based on the weight of said polymer material, ranging from 10 ppm to 3,000 ppm or the maximum solubility limit of said higher fatty acids in said polymer material.

8. The electrophoresis film support according to claim 7, wherein said microporous membrane sheet is made of at least one polymer selected from the group consisting of cellulose esters, polyamides and polyvinyl chloride.

9. The electrophoresis film support according to claim 8, wherein said cellulose esters include cellulose diacetate or cellulose triacetate.

* * * * *